United States Patent [19]
Damme et al.

[11] Patent Number: 5,824,551
[45] Date of Patent: Oct. 20, 1998

[54] METHOD FOR MODULATING CELL APOPTOSIS

[75] Inventors: Jo Van Damme, Brussels; Paul Proost, Heverlee; Frédéric Houssiau; Jean-Christophe Renauld, both of Brussels, all of Belgium

[73] Assignee: Ludwig Institute For Cancer Research, New York, N.Y.

[21] Appl. No.: 541,905

[22] Filed: Oct. 10, 1995

[30] Foreign Application Priority Data

Sep. 12, 1995 [GB] United Kingdom .................. 9518611

[51] Int. Cl.$^6$ .............................. C12N 5/06; C12N 5/08; C12N 5/00; A61K 39/395
[52] U.S. Cl. ...................... 435/375; 435/372.3; 435/335; 424/143.1
[58] Field of Search ................. 435/240.2, 7.21, 435/7.1, 6, 335, 372.3, 375; 424/143.1

[56] References Cited

PUBLICATIONS

Matsue et al. "Reciprocal cytokine–mediated cellular interactions in mouse epidermis: Promotion of gamma delta T–cell growth by IL–7 and TNF–alpha and inhibition of keratinocyte growth by gamma IFN", Invest. J. Dermatol. (1993) 101: 543–548.

Oppenheim et al. "Attractive properties of chemokines and their receptors" Int. J. Immunol. Pharmacol. (1994) 7(3): 219–220.

Burd, et al., "Cloning And Characterization Of A Novel T Cell Activator Gene," *J. Immunol.* 139(9) : 3126–3131 (*Nov. 1, 1987*).

Miller, et al., "A Novel Polypeptide Secreted By Activated Human T Lymphocytes," *J. Immunol.* 143(9) : 2907–2916 (*Nov. 11, 1989*).

Miller, et al., "Sequence And Chromosomal Location Of the I–309 Gene," *J. Immunol.* 145(8) : 2737–2744 (*Oct. 15, 1990*).

Wilson, et al., "Expression and Characterization Of TCA3: A Murine Inflammatory Protein," *J. Immunol.* 145(8) : 2745–2750 (*Oct. 18, 1990*).

Miller, et al., "The human cytokine I–309 is a monocyte chemoattractant," *Proc. Natl. Acad. Sci. USA* 89: 2950–2954 (*Apr. 1992*).

Luo, et al., "Biologic Activities of the Murine β–Chemokine TCA3[1]," *J. Immunol.* 153: 4616–4624 (*1994*).

Laning, et al.,"Inhibition of In Vivo Tumor Growth by the β Chemokine, TCA3[1]," *J. Immunol.* 153: 4625–4635 (*1994*).

Abastado, J. "Apoptosis: function and regulation of cell death", Res. Immun. (1996) vol. 147, pp. 443–456.

Uyttenhove er al. "Functional and structural characterization of P40, a mouse glycoprotein with T–cell growth factor activity", Proc. Natl. Acad. Sci. USA (1988) vol. 85, pp. 6934–6938.

Dive et al. "Analysis and discrimination of necrosis and apoptosis (programmed cell death) by multiparameter flow cytometry", Biochim. Biophys. Acta (1992) vol. 1133, pp. 275–285.

*Primary Examiner*—Jean C. Witz
*Assistant Examiner*—Susan Hanley
*Attorney, Agent, or Firm*—Felfe & Lynch

[57] ABSTRACT

The invention is based upon the newly recognized ability of β chemokines to inhibit cell apoptosis. In particular, apoptosis of T cells is described. The known β chemokines I-309 and TCA-3 are examples of the β chemokines which inhibit apoptosis. One aspect of the invention is the use of these molecules to inhibit apoptosis. A second aspect of the invention is the use of β chemokine inhibitors or antagonists to provoke apoptosis.

9 Claims, 10 Drawing Sheets

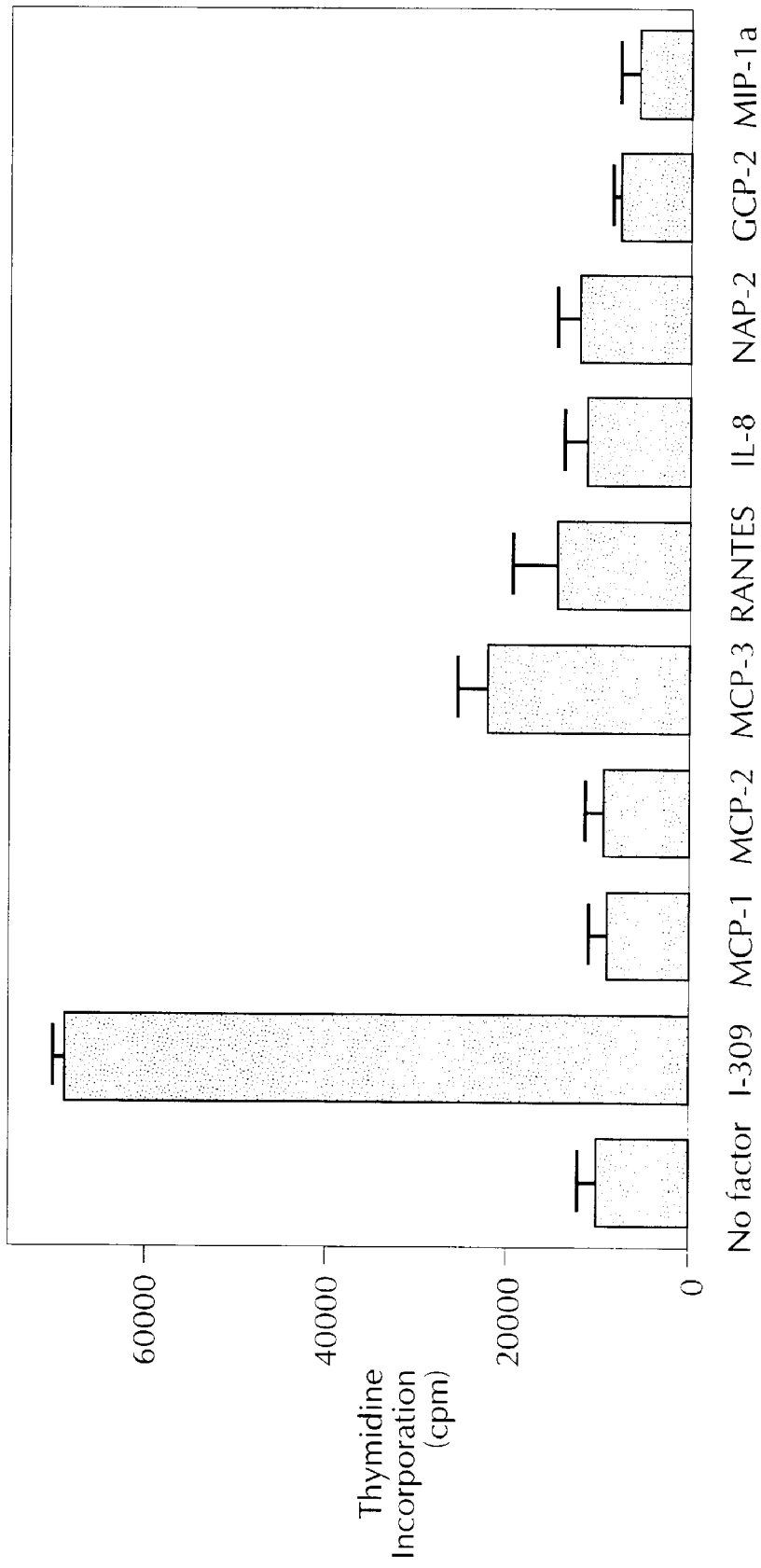

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TCCAGGAATT CCCAAGCCAG ACCAGAA    2

( 2 ) INFORMATION FOR SEQ ID NO: 2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TTGTAGAATT CAAATGTTTA AAGTGCAACA    3

( 2 ) INFORMATION FOR SEQ ID NO: 3:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO: 3:

Lys Ser Met Gln Val Pro Phe Ser Arg Cys Cys Phe Ser Phe Ala Glu
            5                    10                  15

Gln Glu Ile Pro Leu Arg Ala Ile Leu Cys Tyr
           20               25

METHOD FOR MODULATING CELL APOPTOSIS

FIELD OF THE INVENTION

The invention relates to the use of anti-apoptotic factors, especially a mammalian anti-apoptotic factor which is a chemokine. More particularly the invention concerns the use of β chemokines such as I-309, and variants thereof, as anti-apoptotic factors.

BACKGROUND OF THE INVENTION

Chemokines are a subset of cytokines. Cytokines are regulatory proteins secreted by white blood cells and by a variety of other cells in the body. The pleiotropic actions of cytokines include numerous effects on cells in the immune system and the modulation of inflammatory responses ("The Cytokine Handbook", 2nd edition, 1994, ed. A. Thompson, Academic Press, p. 4). Chemokines are a superfamily of proinflammatory cytokines. The chemokine family consists of two branches. In the α chemokines, the first two cysteines are separated by a single amino acid residue (Cys-Xaa-Cys) (e.g., IL-8 and platelet factor-4) whereas, in β chemokines such as TCA-3, the first two cysteines are adjacent (Cys-Cys) (Laning et al., 1994, *J. Immunol.* 153: 4625–4635, incorporated by reference). Molecules in this family share at least 25% amino acid homology, have similar structures, and bind to seven-transmembrane-spanning receptors of the rhodopsin superfamily. The genes encoding the α chemokines are located on human chromosome 4 and the genes encoding the β chemokines are located on human chromosome 17.

Of the β chemokines, the murine protein TCA-3 was originally described by Burd et al. (1987, *J. Immunol.* 139: 3126–3131), which is incorporated by reference in its entirety. Its cDNA was cloned from a T cell helper clone library using a strategy aimed at identifying genes whose expression is induced upon stimulation. Two years later, Brown et al. (1989, *J. Immunol.* 142: 679–687), incorporated by reference, similarly identified a cDNA called P500, which is identical to TCA-3, except for a 99 nucleotide insertion that was generated by alternative splicing in 8% of the cDNA clones that they analyzed. In this paper, TCA-3/P500 was also referred to as SISe (Small Inducible Secreted protein). The sequence of the human I-309 was reported by Miller et al. (1989, *J. Immunol.* 143: 2907–2916), which is incorporated by reference in its entirety. Its cDNA was isolated from an IL-2 dependent T cell line using a similar strategy as reported in the preceding papers for TCA-3 and P500. The sequence of a genomic clone was reported later by Miller et al. (1990, *J. Immunol.* 145: 2737–2744), incorporated by reference in its entirety, and the gene was shown to map to human chromosome 17 as expected for a β chemokine. The genomic structure supports the view that TCA-3 is the murine homologue of I-309.

There are three published reports describing the activity of an example of a β chemokine, that is human I-309, and the murine homologue TCA-3. These are cited herein, and are incorporated by reference. In the first report Wilson et al. (1990, *J. Immunol.* 145: 2745–2750) have produced recombinant murine TCA-3 in CHO cells. They showed that intradermal injection of this material into mouse footpads results in a rapid swelling response, histologically characterized by a local accumulation of neutrophils.

In the second report Miller et al. (1992, *Proc. Natl. Acad. Sci. USA* 89: 2950–2954) produced recombinant human I-309 in CHO cells and showed in vitro that purified I-309 stimulated migration of human monocytes but not neutrophils. I-309 was also shown to induce a transient increase in cytoplasmic free calcium in monocytes but not in neutrophils or lymphocytes. The chemotactic activity required a 10 nM concentration (approximately 150 ng/ml) to be detectable. Maximal effect was found at 100–300 nM and half-maximal activity at approximately 20 nM.

Finally, in the third report Laning et al. (1994, *J. Immunol.* 153: 4625–4635) showed that a mouse tumor expressing TCA-3 lost its tumorigenicity, probably as a result of the anti-tumor immune response following the attraction of neutrophils and macrophages to the tumor site.

As previously mentioned, the human β chemokine I-309 was first described in 1989 by Miller et al. (1989, *J. Immunol.* 143: 2907–2916). The amino acid and cDNA sequences are described therein, along with other structural characteristics, such as a small polypeptide chain including a hydrophobic leader sequence which was thought to be involved in secretion of the corresponding protein. The function of the protein was unknown at that time, but it was suggested that because of the nature of the protein, that is, its relatively small size, secretion by T cells and other certain structural characteristics, it was a cytokine of unknown function. It has now been found that certain β cytokines, including P500 and TCA-3/I-309 demonstrate anti-apoptotic activity, when compared with the known anti-apoptotic agent IL-9, taught as a strong anti-apoptotic factor for thymic lymphoma cell lines. When one considers the effective chemotactic concentration of those proteins discussed infra, one concludes they are strong anti-apoptotic agents. Moreover, given the structural similarities between members of the β chemokine group and also the functional similarities, that is to say distinct chemokines have been shown to bind to the same receptor, it is considered that other members of the β chemokine group will also display anti-apoptotic activity. The following references provide details of the β chemokine group and thus highlight the similarity between members of same. T. J. Schall (1991, *Cytokine* 3: 165–183); and Schall (1994, "The Cytokine Handbook", 2nd edition, ed. A. Thompson, Academic Press, pg. 419–460), incorporated by reference.

"Apoptosis", as used herein, describes one type of cell death. More particularly, it describes programmed cell death where, in the normal course of development, cells die and dismantle in a predictable and orderly fashion. For example, such cells tend to shrink within their membrane and their DNA is broken into nucleosomes for safe removal by cells of the immune system white blood cells in particular.

The scientific community is only now recognizing the clinical importance of apoptosis and therefore only now beginning to invest in research that provides a greater understanding of the process and how the process can be advantageously manipulated in order to either promote, or in some instances, prevent cell death.

There are many examples of disorders and pathologies wherein apoptosis is implicated.

Heart attack is typically characterized by cardiac cell death and it therefore follows that factors that mitigate or prevent this cell death could be used to advantage to protect against the consequences of this condition. In addition, such factors could also be used to advantage in chemotherapy-induced cardiac tissue damage, or in stroke-induced tissue damage or even in kidney failure. The use of such factors would be particularly advantageous where an individual has a history of heart attacks or strokes or even belongs to a family having such a history.

Chemotherapy and radiotherapy also induce other forms of tissue damage and therefore it follows that co-administration or sequential administration of chemotherapy or radiotherapy with an anti-apoptotic factor may be used to advantage in order to mitigate or prevent this widespread damage.

In addition, premature and widespread apoptosis has been implicated in much of the damage associated with acquired immune deficiency syndrome (AIDS). It is thought that apoptosis may be a principal cause of death in uninfected T cells in AIDS patients, leading ultimately to the suppression of the patient's immune system. Thus factors which mitigate or prevent this form of cell death may have a role to play in preventing the damage that the AIDS virus causes in uninfected cells.

Cell death also occurs in instances of ischemia and thus the factors of the invention may also have a role to play in mitigating or preventing apoptosis in ischaemic organs.

In addition to uses of the invention to mitigate or prevent apoptotic activity, it is also apparent that one of the ramifications of the invention is the ability to promote apoptotic activity when desired. For example, the realization that chemokines, and in particular β chemokines such as I-309 and its homologues in other species, have a role to play in preventing apoptosis, can be used to advantage in the manufacture of agents that selectively bind to this factor and thus suppress its anti-apoptotic function, thereby promoting cell death. Naturally occurring, artificial or synthetic agents may be used. For example, antibodies, monoclonal or polyclonal, can be made against the factor of the invention and then used to bind to same with a view to suppressing or annihilating its anti-apoptotic activity. Thus agents which selectively bind with the anti-apoptotic factor of the invention can be used to promote apoptosis and moreover, having regard to the targeted delivery of such agents, can be used selectively to promote apoptosis of diseased tissue.

It may be advantageous to promote apoptosis in order to suppress or reverse tumor development. In this respect, it is of note that anti-apoptotic factors, for example, the product of the bcl-2 gene which encodes a cytoplasmic protein that protects against apoptosis without inducing proliferation by itself, has been shown to be involved in some types of tumours.

In addition to the above, the invention can also be used in drug screening assays. For example, by identifying chemokines, especially β chemokines in different parts of the body, either directly or indirectly, one can map apoptosis in various parts of the body and thus areas, regions or organs most likely to suffer from cell death can be identified for drug screening purposes. In addition, the efficacy of apoptotic promoting agents and also agents acting as β chemokines, in particular I-309 antagonists, can more accurately be determined by observing the activity of such agents in the presence of the factor of the invention. In addition, the invention can also be used to promote cell growth and proliferation and therefore can be used to provide proliferative tissue for drug screening assays.

The full scope of the invention will be understood more fully following review of the disclosure which follows:

DETAILED DESCRIPTION OF PREFERRED EMBODIMENTS

Figure 1A:
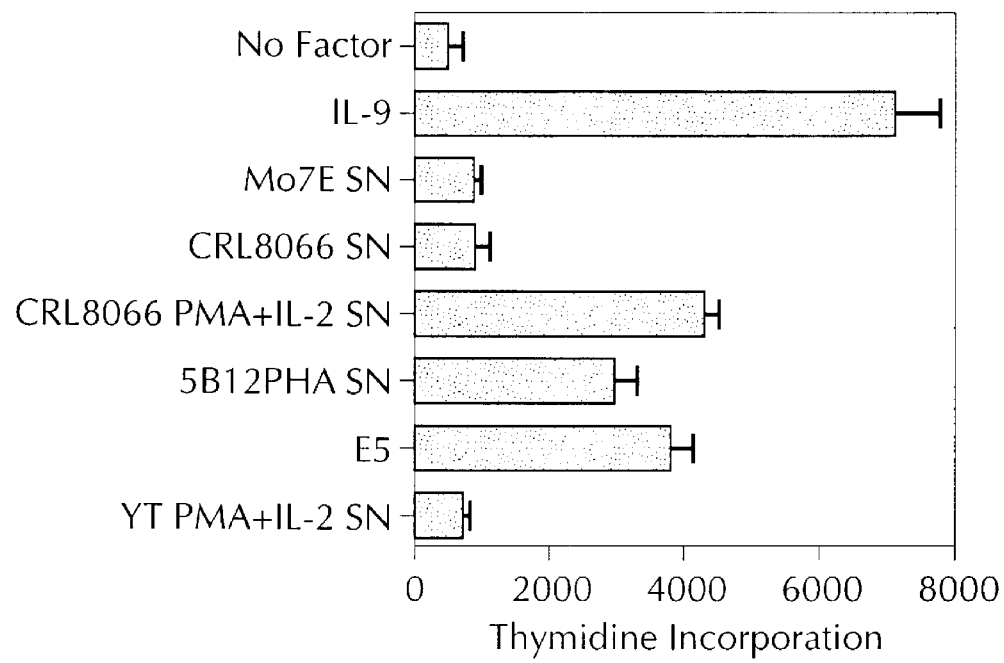
FIG. 1 (A,B) shows anti-apoptotic activity and IL-6 content of various human cell supernatants.

The invention concerns the anti-apoptotic activity of chemokines and in the following examples specific reference is made to the β chemokine I-309. Briefly, the investigations described herein show that murine thymic lymphomas can be made to maintain significant proliferative activity and/or survival in the presence of the factor I-309. The anti-apoptotic activity of the factor is significant in that half maximal anti-apoptotic activity was obtained as a concentration of only 1.6 ng/nl. This concentration is considerably lower (200 times lower) than the concentration required for monocyte chemotactic activity of this molecule suggesting that the primary function of this molecule may be suppression of cell death.

In the following data specific reference is made to BW5147 murine thymic lymphoma. However it is of note that similar activity has also been obtained for two other lymphoma cell lines, i.e., 9T4A2 and NM3T2.

Materials and Methods

Cell cultures, cytokines and other reagents.

Thymic lymphoma cell line BW5147 (Ralph et al., 1973, *J. Immunol.* 110: 1470) was obtained from the American Type Culture Collection (ATCC). NM3T2 cell line was established from a DBA-2 mouse treated with N-Methyl-N-nitrosourea (MNU) and 9T4A2 from a thymic lymphoma that spontaneously arose in an IL-9-transgenic mouse that had lost the IL-9 transgene (Renauld et al., 1994, *Oncogene* 9: 1327). These cells were cultured in Iscove's medium supplemented with 10% fetal calf serum, 1.5 mM L-glutamine, 0.24 mM L-asparagine, 0.55 mM L-arginine and 50 $\mu$M 2-mercaptoethanol.

NK cell leukemia YT and T cell leukemia MoT/CRL8066 (Chen et al., 1983, *Nature* 305: 502–505) were obtained from the ATCC. Mo7E megakaryoblastic leukemia (Avanzi et al., 1988, *Br. J. Haematol.* 69: 359–366) was received from Dr. L. Pegoraro (University of Perugia). 5B12 and E5 are human T cell clones derived from blood lymphocytes of healthy individuals and growing in the presence of PHA or allogenic feeder cells, PHA, IL-2 and IL-4.

Murine IL-9 was produced by expression in baculovirus and purified by affinity chromatography in our laboratory. Saturating doses (200 U/ml) were used in every experiment. Recombinant TCA-3 was purchased from R&D laboratories and Pertussis Toxin was from BIOMOL (Plymouth Meeting, Pa.). Dexamethasone (DEX) was obtained from Sigma and used at 0.25 $\mu$M concentration in all experiments. The rat anti-murine IL-6 receptor, 15A7 (Coulie et al, 1990, *Curr. Top. Microbiol. Immunol.* 166: 43–46), and mouse anti-human IL-6, AH64 (Brailly et al, 1994, *Clin. Chem.* 40: 116–123), antibodies were used at 50 ug/ml and at 1/100 dilution of ascites fluid, respectively.

The 7TD1 bioassay used to measure IL-6 was performed as described previously (Van Snick et al., 1986, *Proc. Natl. Acad. Sci. USA* 83: 9679–9683). Briefly, $2 \times 10^3$ 7TD1 cells were seeded in microwells and cultured for 4 days in the presence of serial dilutions of the supernatants. The proliferation was evaluated by calorimetric determination of hexosamindiase levels as described by Landegren et al., 1984, *Cytokine* 3: 165–183.

Anti-apoptic bioassays

Cell viability was determined using a propidium iodide incorporation assay as described (Lee et al., 1993, *J. Immunol.* 151: 5208). Briefly, cells were incubated for 30 minutes with propidium iodide (125 $\mu$g/ml) at room temperature before FACS analysis with a FACScan flow cytometer (Becton-Dickinson). Under these conditions, dead cells are brightly stained while live cells are not. A minimum of 5000 cells were counted per sample.

To test the influence of cytokines on proliferation in the presence of DEX, BW5147 cells were incubated in triplicate microtiter wells in the presence of DEX at a final $0.25 \times 10^{-6}$ molar concentration with or without cytokines, in a 200 $\mu$l volume. Cultures were pulsed 2–4 days later for 6 h with 0.5 $\mu$Ci $^3$H-thymidine. Alternatively, cell proliferation was measured by an hexosaminidase assay, as described (Uyttenhove et al., 1988, *Proc. Natl. Acad, Sci, USA* 85: 6934).

Purification procedures

MoT/CRL8066, a hairy cell leukemia T type, was cultured in RPMI-1640 medium supplemented with 10% heat-inactivated (56° C., 30 min) FCS, 0.55 mM L-arginine, 0.24 mM L-asparagine, and 1.25 mM L-glutamine. For the production of large batches, cells were washed, resuspended in the same medium containing 5% FCS and stimulated at a concentration of $5 \times 10^5$ cells/ml with PMA (50 ng/ml) (Sigma). After heating for 30 minutes at 57° C. in order to inactivate HTLV-II virus, supernatants were buffered with sodium phosphate, pH 7.0, and ammonium sulfate was added to a final concentration of 1.2M. This preparation was chromatographed on a Phenyl-Sepharose Fast flow column (Pharmacia) at 8 ml/min. After a 500 ml wash with 1.2M ammonium sulfate, active material was recovered by a two-step elution at 3 ml/ml with 1 liter of 0.7M and 0.5M ammonium sulfate.

After concentration, the material was transferred into a sodium acetate 50 mM, pH 5.5 buffer containing 0.01% (vol/vol) Tween 20 before cation exchange chromatography on a Sulfo-Propyl Sepharose Fast flow gel (Pharmacia) at 3 ml/min. After washes with 100 ml of the same buffer and 140 ml of 0.3M NaCl in the same buffer, elution was performed with a 300 ml linear gradient of NaCl to 1M, the active material being eluted at 0.5 to 0.75M NaCl.

The active fractions were concentrated, transferred into 50 mM phosphate buffer, pH 7.0, containing 1M NaCl and 0.01% (vol/vol) Tween 20 and fractionated on a Superdex 70 size-exclusion column (Pharmacia). The active material (eluted with apparent molecular weight of 12–16 kD) was transferred into 100 mM $Na_2HPO_4$ buffer pH 7.0 containing 1M $Na_2SO_4$ and loaded onto a TSK-phenyl column (LKB, Bromma, Sweden) at 0.5 ml/min. After a 5 min wash in the starting buffer, elution was carried out at 0.5 ml/min with a linear gradient of a 1/l mixture of sodium phosphate (0.1M, pH 7.0) and ethylene glycol (from 0 to 60% in 30 min), the active material being eluted at 30% of this buffer.

The active fractions were transferred into sodium acetate 50 mM, pH 5.5 buffer containing 0.01% (vol/vol) Tween 20 before cation exchange chromatography on a Sulfo-Propyl Resource S column (Pharmacia) at 0.8 ml/min. Elution was performed at 0.8 ml/min with a 10 min linear gradient of NaCl to 0.2M, followed by a 30 min gradient to 0.4M NaCl, the active material being eluted at 0.3M NaCl.

The most active fraction was adjusted to contain 0.1% trifluoroacetic acid and further analyzed by reverse phase chromatography on a Vydack C4 column. The column was developed at 0.8 ml/min with a 40 min linear gradient from 8 to 56% acetonitrile in 0.1% trifluoroacetic acid. Fractions were collected in Eppendorf tubes containing 5 $\mu$l of Tween 20 (1% in water), lyophilized and resuspended in $Na_2HPO_4$ buffer (50 mM, pH 7.0) before testing the anti-apototic activity.

cDNA cloning and COS cell transfections

The coding sequence of the human I-309 cDNA was amplified by RT-PCR using total RNA extracted from a PHA activated T cell clone (E5). Reverse transcription was performed on 5 $\mu$g total RNA with an oligo(dT) primer, cDNA corresponding to 200 ng of total RNA was amplified for 30 cycles by PCR with the following specific primers into which an EcoRI site was inserted: sense 5'-TCCAGGAATTCCCAAGCCAGACCAGAA-3' (SEQ ID NO:1) (from position 19 of the cDNA sequence), anti-sense 5'-TTGTAGAATTCAAATGTTTAAAGTGCAACA-3' (SEQ ID NO:2) (from position 503 of the cDNA sequence). The amplification product was digested by EcoRI and cloned in the pCDSRα expression vector (Takebe et al, *Mol. Cell Biol.* 8: 466–472 1988) The nucleotide sequence was determined by the dideoxynucleotide chain termination method using the Taq cycle sequencing system (Amersham) with $\gamma^{32}$P-ATP labelled oligonucleotides, and no difference was observed when compared to the published I-309 sequence (Genbank Accession Number M57502) (Miller et al., 1989, *J. Immunol.* 143: 2907–2916).

Anti-apoptotic activity and IL-6 content of various human cell supernatants. (FIG. 1 (A,B))

A: For the anti-apoptotic assay, BW5147 cells ($10^3$/well) were incubated for 3 days in the presence of dexamethasone (DEX) (0.25 $\mu$M) with or without murine IL-9 (200 U/ml) or 3.3% of supernatant from the Mo7E megakaryoblastic leukemia cell line, MoT/CRL8066 T cell leukemia cell line (stimulated or not with PMA and IL-2 for 3 days) the YT NK cell leukemia stimulated with PMA and IL-2 or 10% of T cell clone supernatants (5B12 and E5). Cell proliferation was evaluated by measuring thymidine incorporation and standard deviations were calculated from triplicate cultures. In the absence of DEX, thymidine incorporation was 117, 947±7,122 cpm.

B: The IL-6 content of the supernatants was measured by the 7TD1 bioassay as described. 1 U/ml corresponds to the concentration required for half-maximal proliferation (approximately 5 pg/ml for human IL-6).

Figure 2:
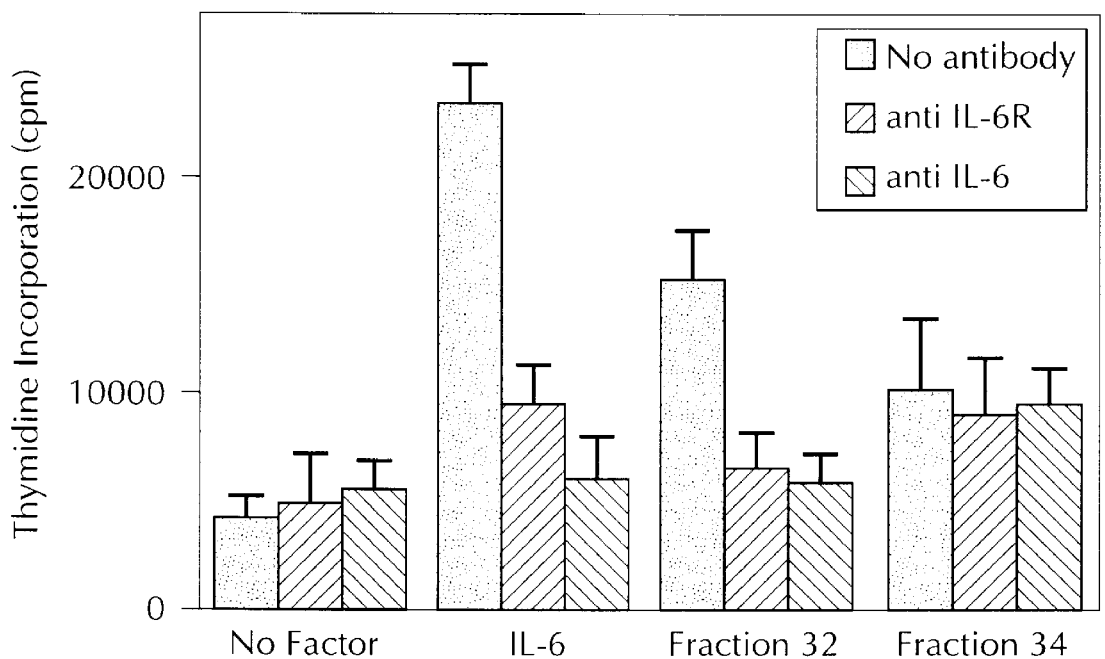
FIG. 2 shows inhibition by anti-IL-6 antibody of the activity of some but not all fractions of activated CRL8066-MoT supernatants.

Inhibition by anti-IL-6 antibody of the activity of some but not all fractions of activated CRL8066-MoT supernatants. (FIG. 2)

BW5147 cells ($10^3$/well) were incubated for 3 days in the presence of DEX (0.25 $\mu$M) with or without human IL-6 (500 U/ml) or aliquots from elution fractions of the Superose chromatography. The rat anti-murine IL-6 receptor, 15A7, and the mouse anti-human IL-6 antibodies were used at 50 $\mu$g/ml and at 1/100 dilution of ascites fluid, respectively. Cell proliferation was evaluated by measuring thymidine incorporation and standard deviations were calculated from triplicate cultures.

Figure 3:
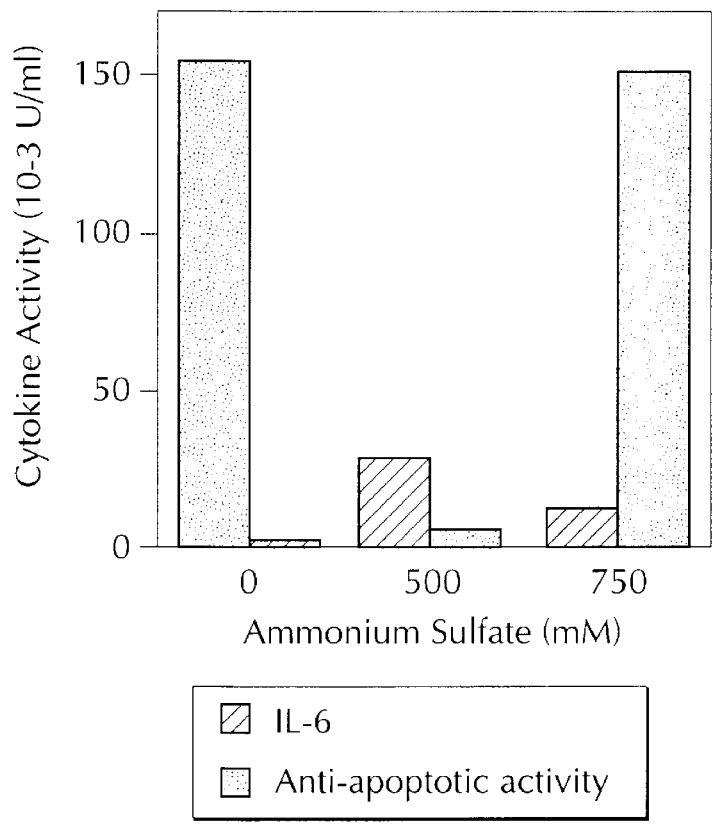
FIG. 3 shows distinct fractionation of IL-6 and anti-apoptotic activity on phenyl sepharose.

Distinct fractionation of IL-6 and anti-apoptotic activity on phenyl sepharose. (FIG. 3)

Supernatants from PMA-stimulated MoT/CRL8066 cells were heated for 30 minutes at 57° C. in order to inactivate HTLV-II virus, buffered with sodium phosphate, pH 7.0 before ammonium sulfate was added to a final concentration of 1.2M and loading on a Phenyl-Sepharose Fast flow column (Pharmacia). After appropriate washing, a three step elution was performed with 0.75, 0.5, and 0.0M ammonium sulfate and the activity of the fractions was evaluated in the 7TD1 assay for IL-6 and in the BW5147 anti-apototic assay as described in Material and Methods.

Figure 4A:
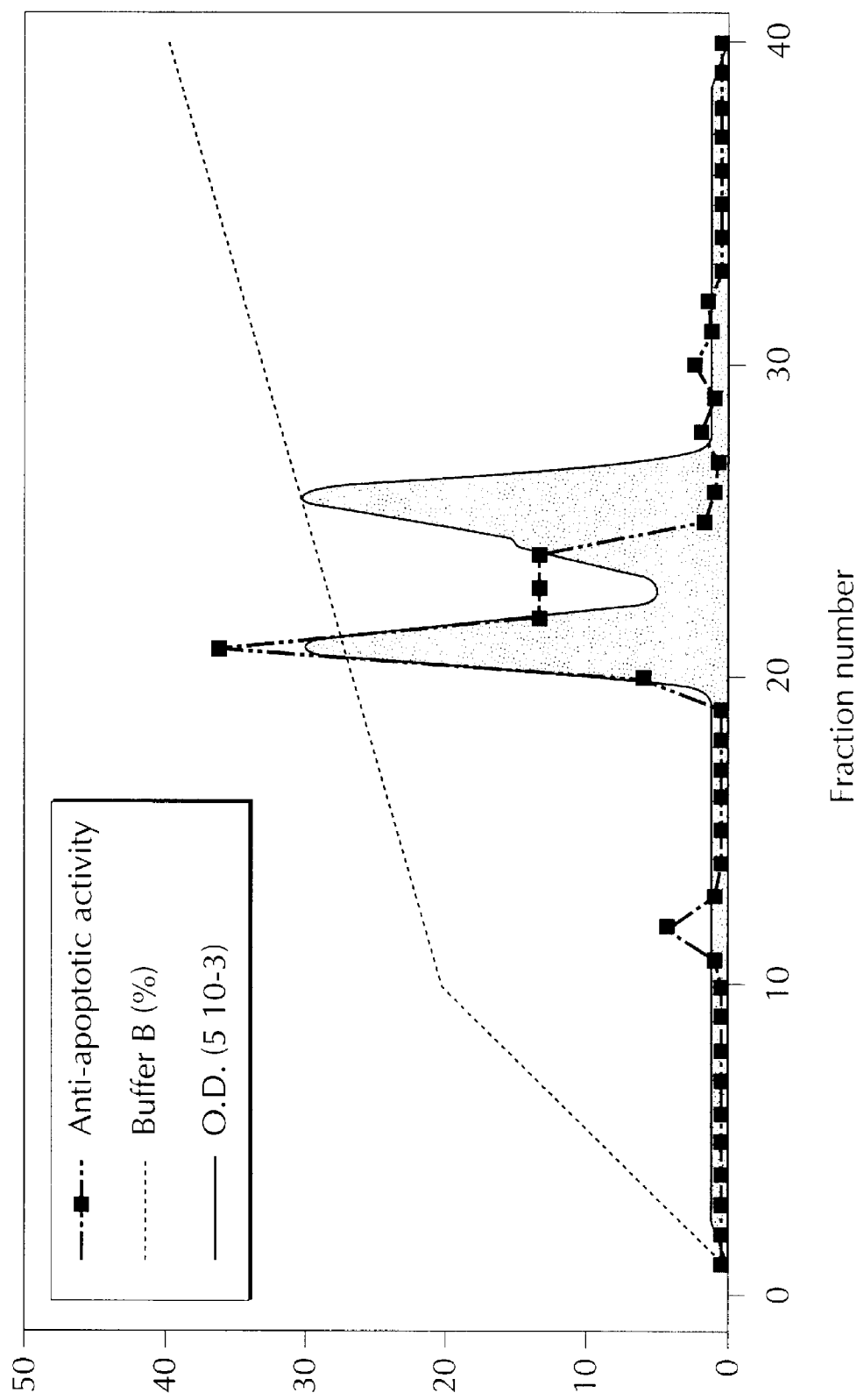
FIG. 4 (A,B) shows final purification of anti-apoptotic factor on a Resource S column and SDS PAGE gel.
Figure 4B:
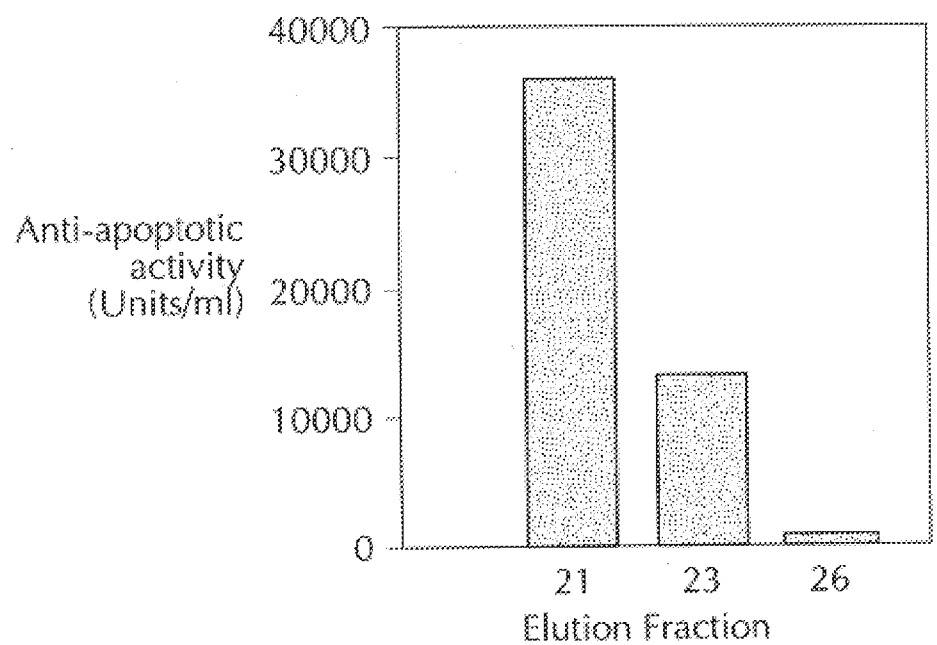
Figure 4C:
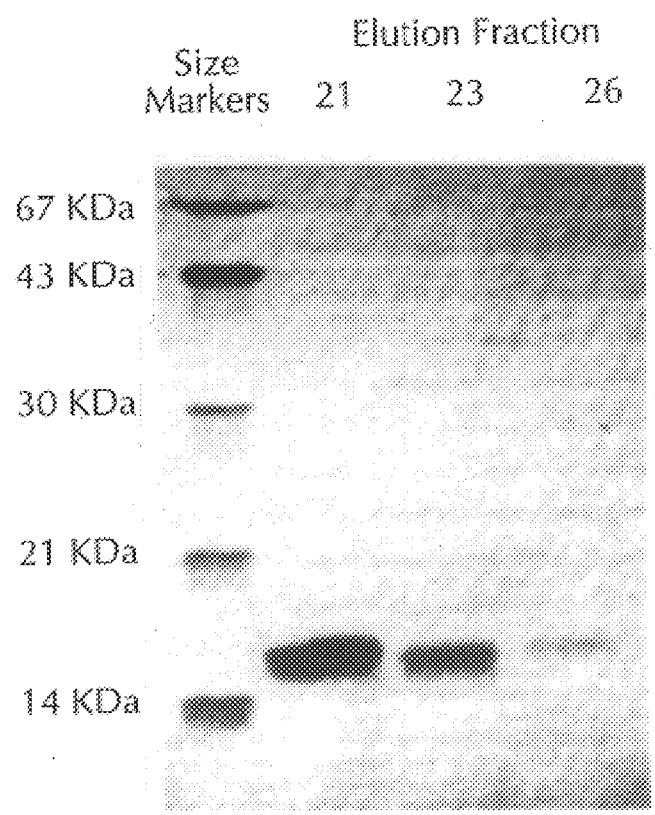

Final purification of anti-apoptotic factor on Resource S column and SDS PAGE gel. (FIG. 4 A,B)

A: After three successive steps of separation on a phenyl-sepharose gel, Sulfo-Propyl column and Superdex size exclusion column, the active fractions were fractionated by cation-exchange chromatography on a Sulfo-Propyl Resource S column. Elution was performed by a NaCl gradient as shown by the dotted line (Buffer B=1M NaCl). The optical density (280 nm) of the eluted material (strippled area) and the anti-apoptotic activity (closed squares) are shown. 1 U/ml of anti-apoptotic activity is arbitrarily defined as the concentration giving half-maximal protection against DEX in the BW5147 bioassay described in Materials and Methods.

B: SDS PAGE analysis of aliquots from pools of active fractions from the chromatography shown in A. The molecular weight of size markers are indicated to the right.

Anti-apoptotic and chemotactic activities of purified I-309. (FIG. 5 A,B)

A: BW5147 cells ($10^3$/well) were incubated for 3 days in the presence of DEX (0.25 $\mu$M) with or without serial dilutions from fraction 21 of the Resource S chromatography shown in FIG. 4. Cell proliferation was estimated by a colorimetric hexosaminidase assay. I-309 concentrations were deduced from the micro-sequencing analysis.

B: The same method was used in a chemotactic assay using the human THP1 monocytic cell line (left panel). Results are indicated as chemotactic indices. Purified human MCP-3 was used as a positive control for this assay (right panel).

Figure 6A:
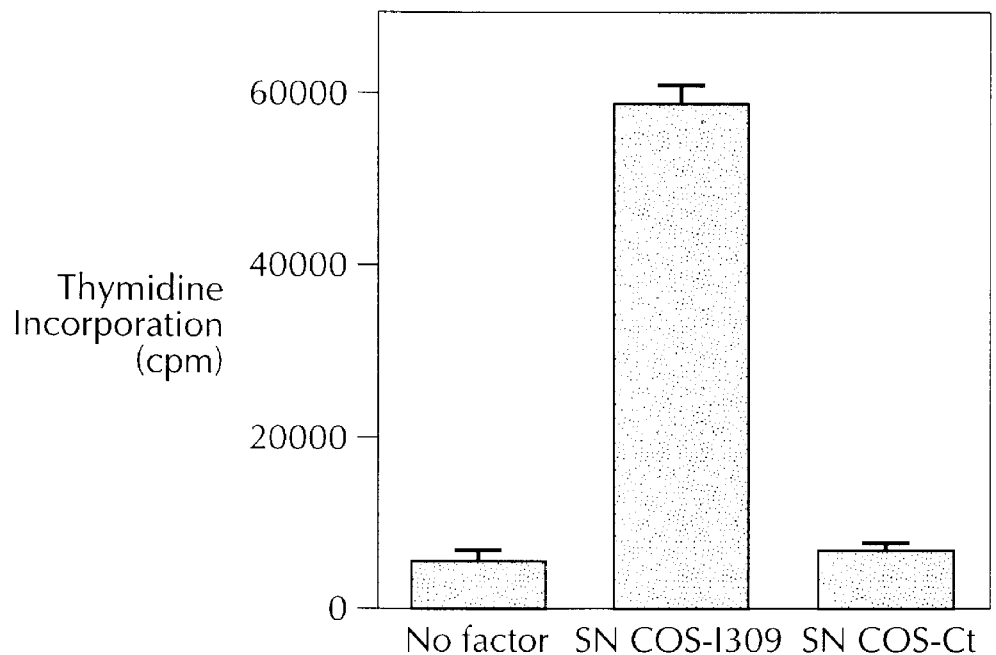
FIG. 6 (A,B) shows proliferation of BW5147 cells induced by recombinant I-309 expressed in COS cells and by recombinant TCA-3 in the presence of dexamethasone.
Figure 6B:
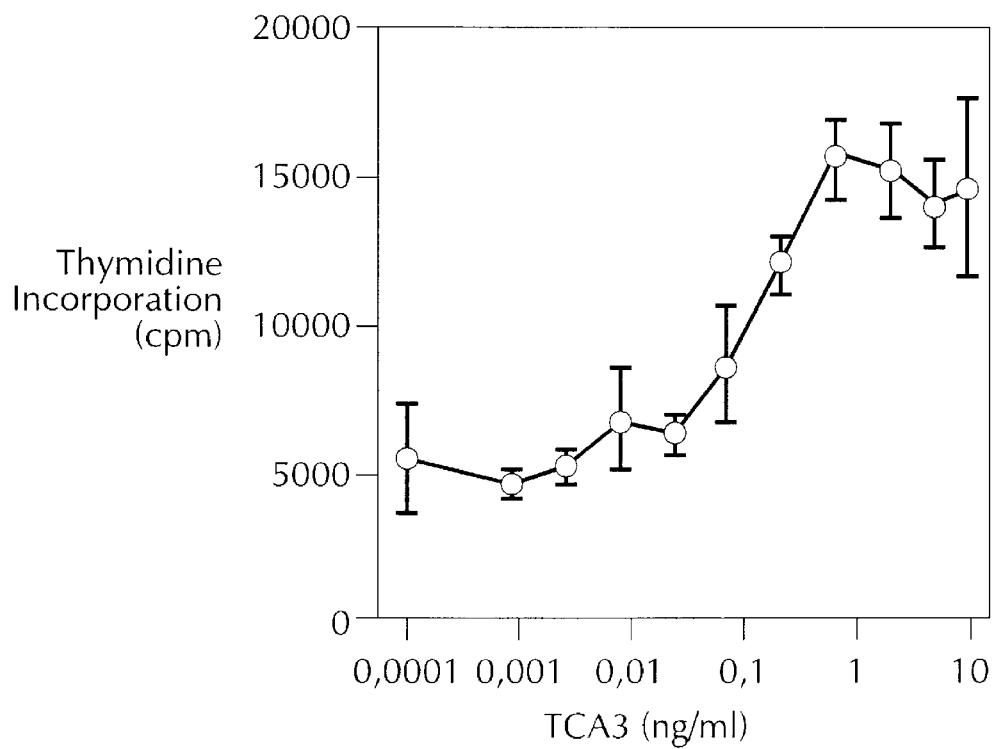

Proliferation of BW5147 cells induced by recombinant I-309 expressed in COS cells and by recombinant TCA-3 in the presence of dexamethasone. (FIG. 6 A,B)

A: BW5147 cells ($10^3$/well) were incubated for 3 days in the presence of DEX (0.25 $\mu$M) with or without a 1/15 dilution of supernatant from COS cells transfected with the I-309 cDNA or a control plasmid. Cell proliferation was evaluated by measuring thymidine incorporation and standard deviations were calculated from triplicate cultures.

B: The anti-apoptotic activity of serial dilutions of recombinant murine TCA-3 was measured as described in A.

Figure 7A:
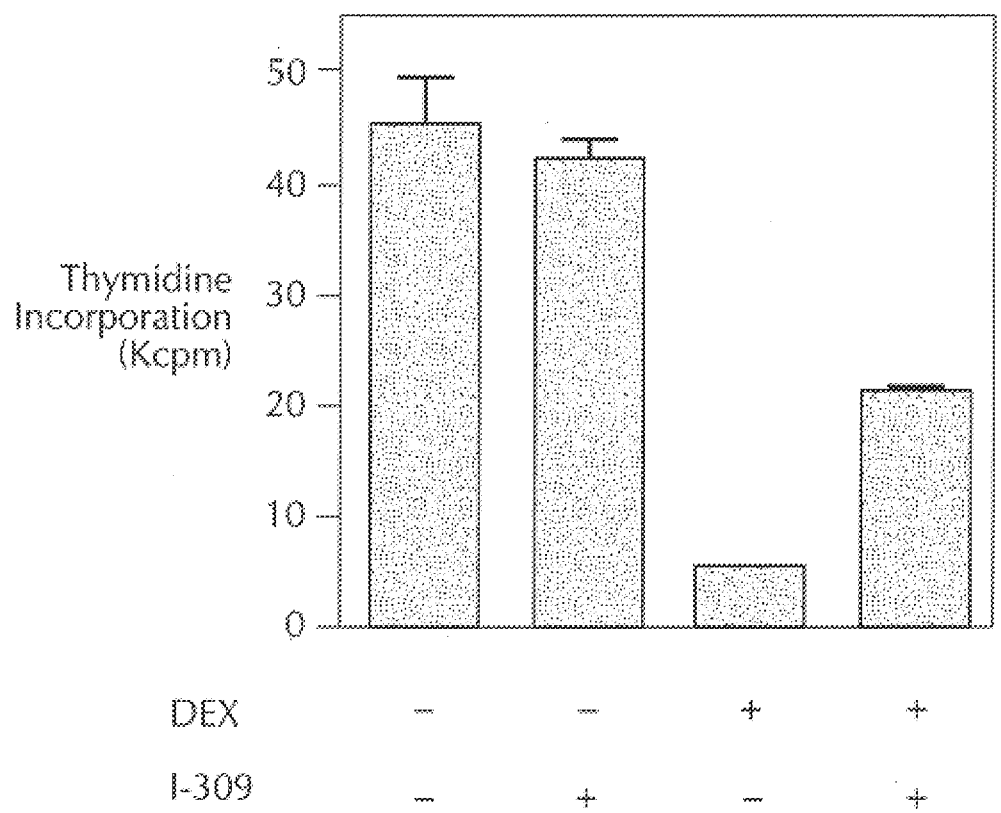
FIG. 7 shows inhibition of I-309 by Pertussis toxins, i.e. induced proliferation of BW5147 cells in the presence of dexamethasone.
Figure 7B:
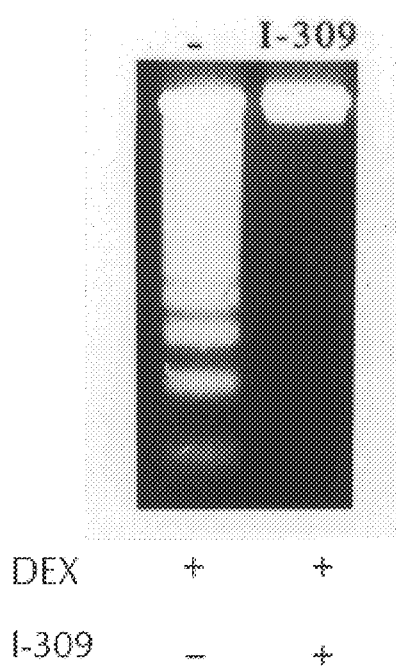

Inhibition by Pertussis toxin of I-309-induced proliferation of BW5147 cells in the presence of dexamethasone. (FIG. 7)

BW5147 cells ($10^3$/well) were incubated for 3 days in the presence of DEX (0.25 $\mu$M) with or without a 1/15 dilution of supernatant from COS cells transfected with the I-309 cDNA or a saturating concentration of mIL-9 (200 U/ml). Cell proliferation was evaluated by measuring thymidine incorporation and standard deviations were calculated from triplicate cultures.

Figure 8A:
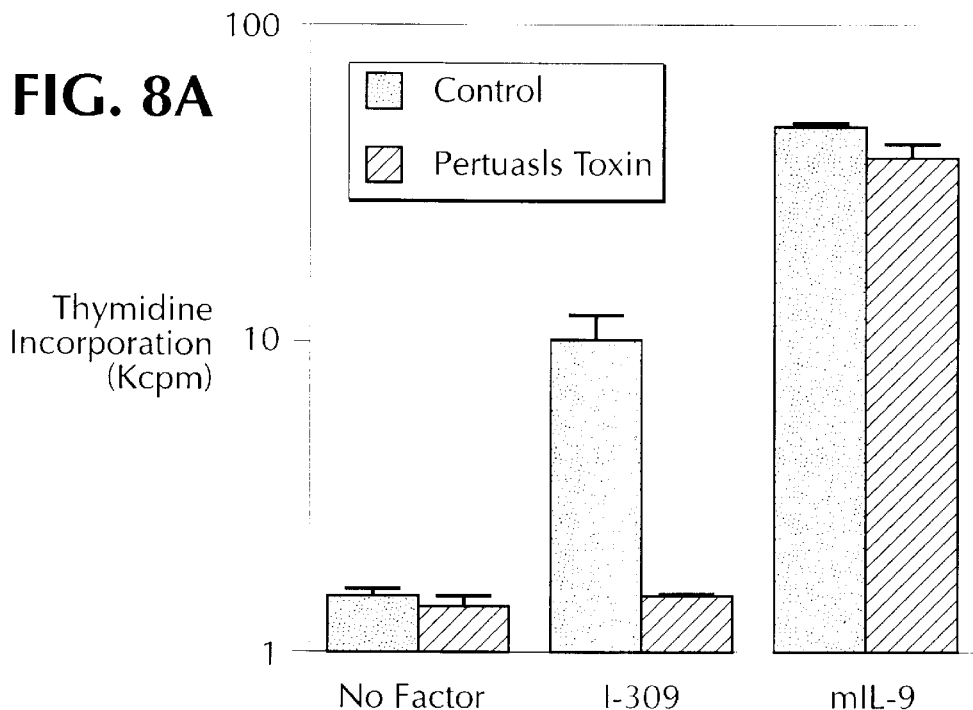
FIG. 8 shows anti-apoptotic activity of I-309 for 9T4A2 and NM3T2 thymic lymphoma cell lines exposed to dexamethasone.
Figure 8B:
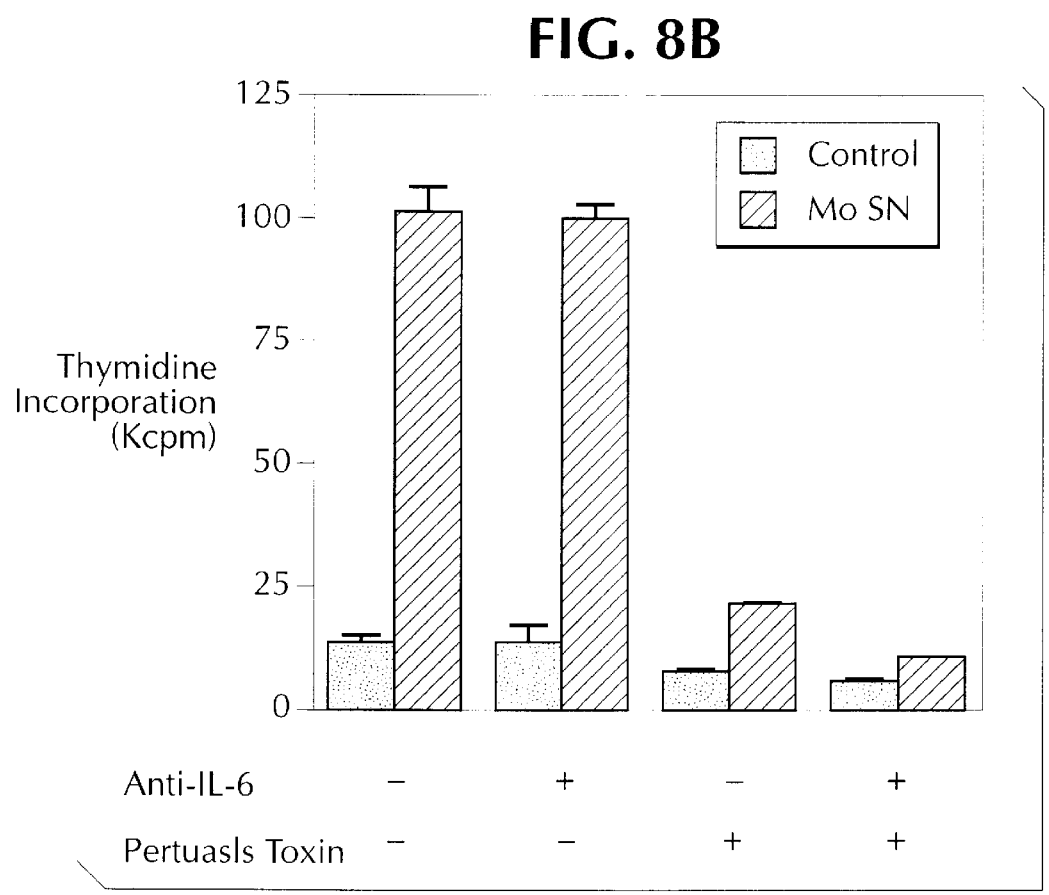
Figure 9A:
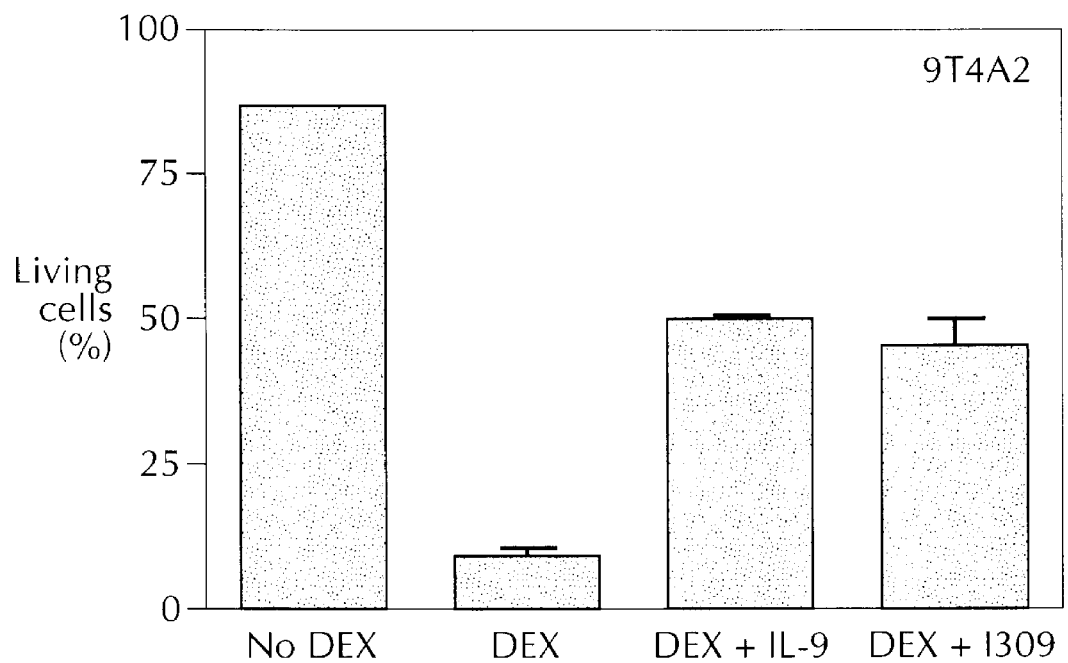
Figure 9B:
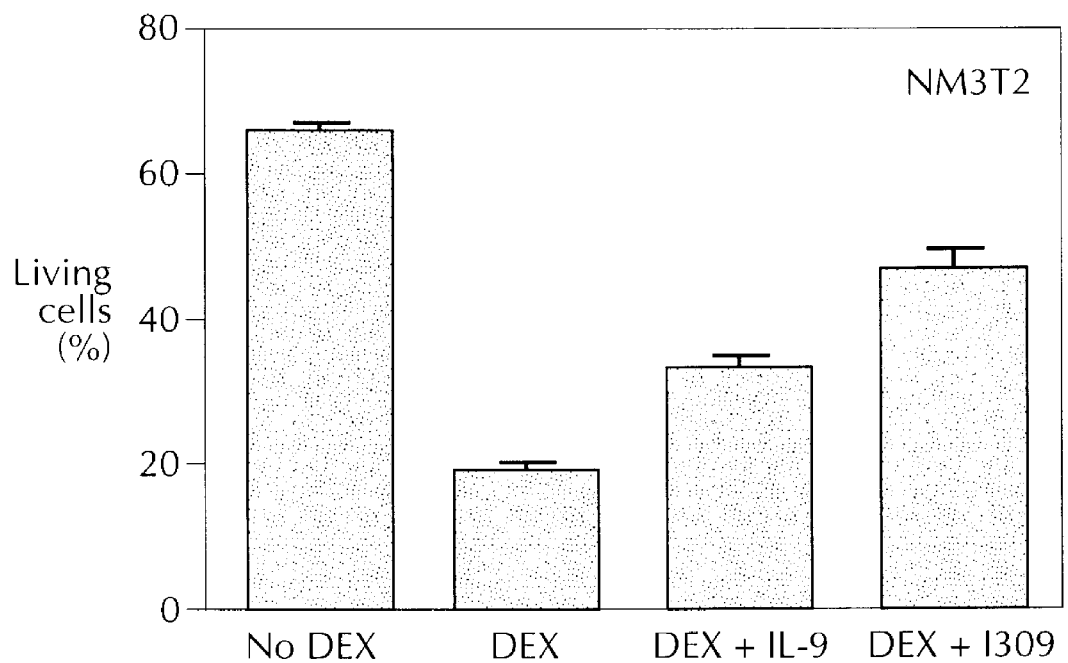

Anti-apoptotic activity of I-309 for 9T4A2 and NM3T2 thymic lymphoma cell lines exposed to dexamethasone. (FIG. 8)

Cells were incubated with dexamethasone in the presence or absence of I-309 (100 U/ml) or IL-9 (500 U/ml) for 20 h. Cell viability was measured by FACS analysis after staining with propidium iodide as described in Material and Methods.

Results

Figure 1B:
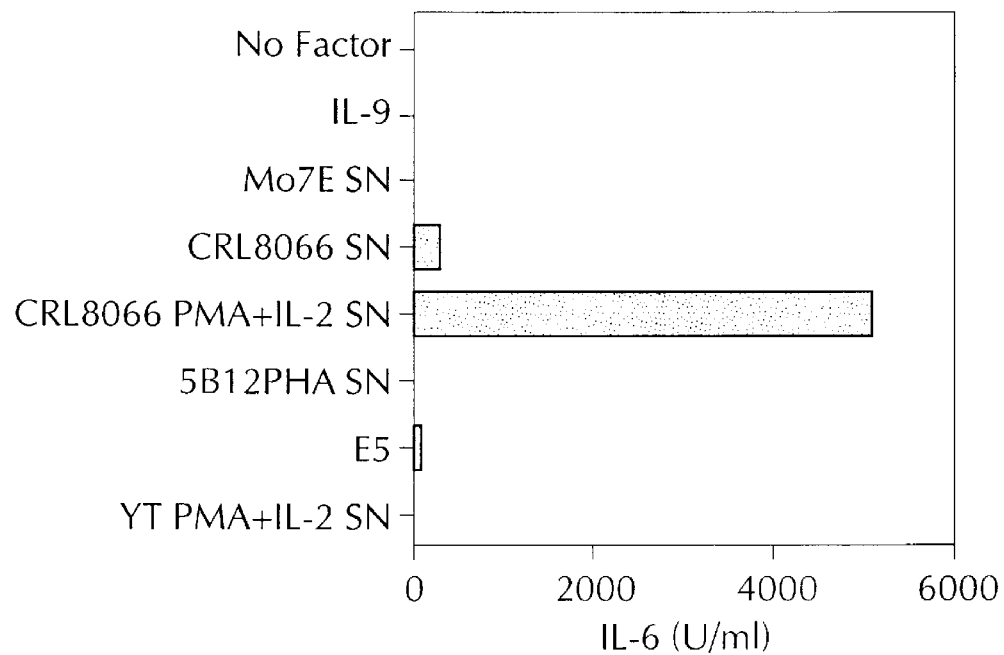

Identification of anti-apoptotic activity distinct from IL-6 in human T-cell supernatants In a previous report, it had been shown that the murine thymic lymphoma BW5147 is protected against dexamethasone-induced apoptosis by IL-9, IL-4 and to a lesser extent by IL-6. By contrast, IL-1, IL-2, IL-7, IL-10, IL-13, IFN$\gamma$ and TNF$\alpha$ were not active in this assay (Renauld et al, 1995, Blood 85: 1300–1305), as well as IL-3, IL-11, LIF, GM-CSF and Steel Factor (unpublished data). Since human IL-9 and human IL-4 are not active on murine cells, we used this bioassay to screen a series of human supernatants for another anti-apoptotic activity. Since human IL-6 is active on murine cells, we simultaneously measured the IL-6 titers of these supernatants. As shown in FIG. 1A, proliferation of BW5147 cells cultured in the presence of dexamethasone was observed with murine IL-9 but also with some human cell supernatants such as those from activated T cell leukemia (CRL8066-MoT) or from CD4+ T cell clones (5B12, E5). Interestingly, this activity was not strictly correlated with the concentration of IL-6 in these supernatants as shown in FIG. 1B. Although the most potent supernatant (activated CRL8066-MoT) contained large amounts of IL-6, other active samples (5B12 and E5 supernatants) were essentially devoid of IL-6, suggesting that a factor distinct from the previously checked cytokines could protect BW5147 cells against dexamethasone-induced apoptosis.

To further discriminate this putative factor from IL-6, CRL8066-MoT cell supernatants, concentrated by adsorption to sulfopropyl sephadex beads, were chromatographed on a size exclusion gel by FPLC. This experiment showed that a factor smaller in size than IL-6 and not inhibited by anti-human IL-6 or anti-mouse IL-6 receptor antibodies was also active in this assay (FIG. 2). This conclusion was confirmed by results obtained in a hydrophobic interaction chromatography on phenyl sepharose. As shown in FIG. 3, the major anti-apoptotic activity was eluted at 0.75M ammonium sulphate, while IL-6 was recovered only at 0.0M salt.

Purification and micro-sequencing of the factor responsible for the anti-apoptotic activity CRL8066-MoT cells were produced by stimulating the cells at a concentration of 500,000 cells/ml with PMA at 50 ng/ml for 3 days in medium containing 5% FCS. After chromatography on a Phenyl-Sepharose column, the material was fractionated on a cation exchange gel at pH 5. The active fractions were transferred into a neutral phosphate buffer containing 1M NaCl and a $10^{-4}$ dilution of Tween 20, and subjected to gel filtration chromatography. The anti-apoptotic activity eluted with an apparent molecular weight ranging from 10 to 20 kD with a peak at 15 kD. Further fractionation was carried out by hydrophobic interaction chromatography on a TSK phenyl column from which the active material eluted at 0.7M Na$_2$SO$_4$ and 15% ethylene glycol. Finally, the active fractions were purified to homogeneity on a Resource S cation exchange column by FPLC. The results of this last chromatography step are shown in FIG. 4, together with the corresponding SDS PAGE analysis of the active fractions.

The purity of this preparation was confirmed by the fact that HPLC analysis of the most active fraction (fraction 21, see FIG. 4) showed a single protein peak, from which the anti-apototic activity was retrieved. Sequencing of 30 pmoles of protein from fraction 21 of the Resource S column (FIG. 4) generated the following 27 amino acid sequence : NH$_2$-Lys-Ser-Met-Gln-Val-Pro-Phe-Ser-Arg-Cys-Cys-Phe-Ser-Phe-Ala-Glu-Gln-Glu-Ile-Pro-Leu-Arg-Ala-Ile-Leu-Cys-Tyr, (SEQ ID NO:3) which was completely identical to amino acids 1 to 27 of the β-chemokine I-309 (Miller et al, 1989, *J. Immunol.* 143: 2907–2916; Miller et al., 1990, *J. Immunol* 145: 2737–2744).

Comparison of the specific activity of I-309 in chemotactic and anti-apoptotic in vitro assays.

Figure 5A:
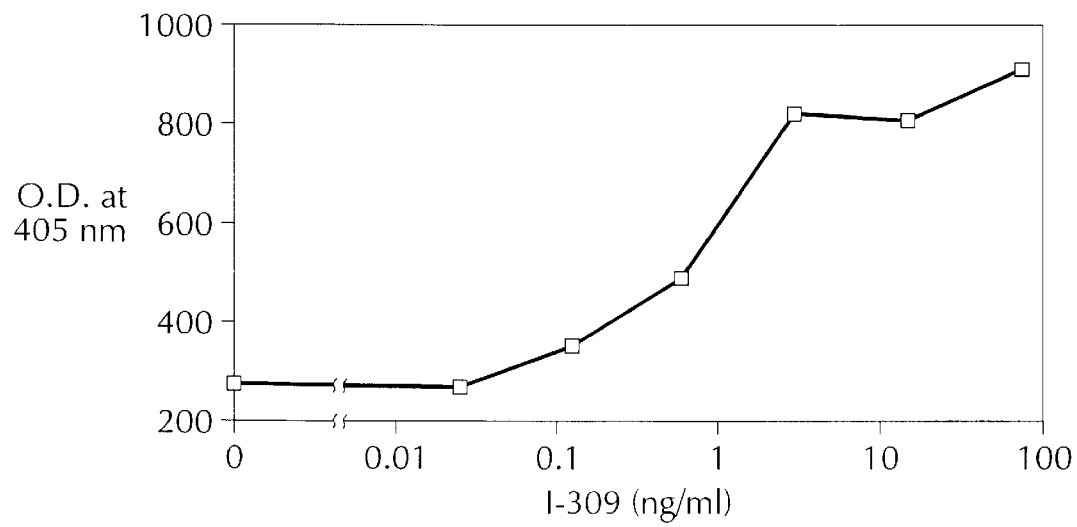
FIG. 5 (A,B) shows the anti-apoptotic and chemotactic activities of purified I-309 on BW5147 cells in the presence of dexamethasone (panel A) and on human THP1 monocytic cells (panel B).

Based on concentrations deduced from the microsequencing analysis, the specific activity of purified I-309 was measured in the anti-apoptotic assay. Maximal protective activity for BW5147 cells was reached at a 3 ng/ml concentration (FIG. 5A). If, in this assay, one defines one unit as the concentration required to give half-maximal protection against dexamethasone, one unit would be equivalent to 1.65 ng/ml (approximately 100 pM). Interestingly, this specific activity was found to be in a similar range as that of murine IL-4 in the same bioassay (Renauld et al., 1995, *Blood* 85: 1300–1305).

Figure 5B:
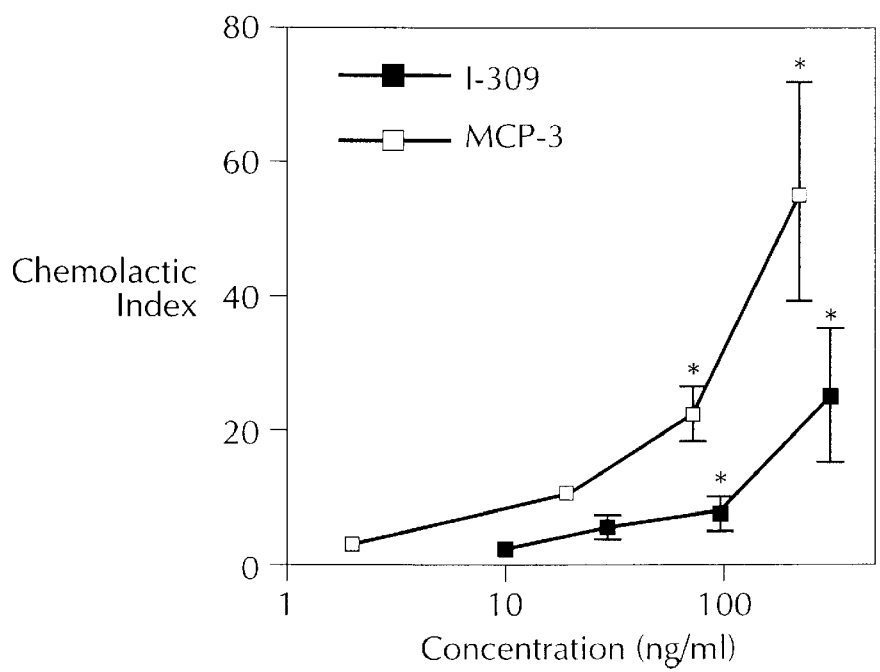

The same purified material was tested in a chemotactic assay using the human monocytic cell line THP1. As shown in FIG. 5B, significant chemotactic responses to I-309 required considerably higher concentrations. Similar results were obtained using normal monocytes (data not shown). Taken together, these data indicate that the anti-apoptotic effect reported here is a much more sensitive assay and that I-309 might be in fact much more effective in vivo as an anti-apoptotic agent than as a chemotactic factor.

Anti-apoptotic activity of recombinant I-309 and TCA-3.

To formally establish that the anti-apoptotic activity observed with our purified material can be ascribed to I-309 cDNA was amplified by RT-PCR from a PHA activated T cell clone, inserted into an expression vector and transfected into COS-7 cells. As shown in FIG. 6, the supernatant from I-309-transfected COS cells strongly stimulated proliferation of BW5147 cells in the presence of dexamethasone, while control COS cell supernatant was totally inactive. In addition, baculovirus derived TCA-3, considered as the murine homologue of I-309, had a similar activity with half-maximal effect observed at approximately 0.5 ng/ml.

Inhibition of the anti-apoptotic activity of I-309 by Pertussis toxin.

The receptor molecule for I-309/TCA-3 has not yet been identified. However, every chemokine receptor identified so far consist in a transmembrane protein with seven transmembrane domains that transduce the signal through G proteins. Since Pertussis toxin is known to interfere with the activation mediated by a subset of these receptors, we analysed the effect of this molecule on the anti-apoptotic activity of I-309. As indicated in FIG. 7, when BW5147 cells were exposed to dexamethasone in the presence of recombinant I-309, Pertussis toxin completely abrogated the proliferation induced by I-309 in the presence of DEX. By contrast, Pertussis toxin did not inhibit the IL-9-induced cell proliferation, demonstrating that completely distinct mechanisms of signal transduction are involved. These results also suggest that chemokine receptors linked to G proteins may play an unexpected role in the control of cell survival under apoptosis-promoting conditions.

Anti-apoptotic activity of I-309 on other thymic lymphoma cell lines.

To see whether the anti-apoptotic activity of I-309/TCA-3 can be extended to other thymic lymphoma cell lines, we tested the activity of purified I-309 on two other dexamethasone-sensitive cell lines, 9T4A2 and NM3T2, by measuring cell death 20 hours after exposure to dexamethasone. As shown in FIG. 8, I-309 was found to be as potent as IL-9 in inhibiting apoptosis in these cells. These results suggest that the anti-apoptotic activity of I-309 may be a common phenomenon for these types of tumor lines.

The foregoing examples and disclosure describe the invention, which is a method of modulating cell apoptosis. In one aspect of the invention, the modulation involves the inhibition of cell apoptosis by administering an amount of a β chemokine to a cell sample, in an amount sufficient to inhibit apoptosis of cells in said sample. Especially preferred are proteins which have I-309 activity including mammalian analogous of I-309, such as TCA-3, P500, and so forth, as well as anti-apoptotic fragments of these β chemokines. Especially preferred are methods of inhibiting T cell apoptosis, using the β chemokines in the manner described. "Effective amount" as used herein refers to any amount of the β chemokine sufficient to inhibit cell apoptosis. Preferably, the amount of β chemokine used will range from about 0.1 ng/ml up to about 100 ng/ml. Most preferably, the amount dosed will range from about 1.0 ng/ml to about 3.0 ng/ml. When used in vivo, the protein may be administered in accordance with any of the standard therapeutic regimes, such as orally, intravenously, intramuscularly, subcutaneously, intranasally, or intradermally, with or without a carrier, adjuvant, or additional material to protect the active ingredient from degradation by normal physiological processes. When used in vitro, solutions, emulsion, etc. may be used to facilitate the applications of the material.

One may also inhibit cell apoptosis, as indicated herein, by administering antagonists of β chemokines, such as I-309 antagonists, to a subject. As indicated, these antagonists may be antibodies, such as polyclonal or monoclonal antibodies, soluble forms of the I-309 receptor, and also derivatives of the β chemokines which share sufficient structural similarities with the β chemokines to bind to β chemokine receptors, but sufficiently different so as to be apoptotically inert.

Other aspects of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for inhibiting apoptosis, comprising administering to a cell containing sample an amount of an apoptosis inhibiting I-309 β chemokine sufficient to inhibit apoptosis of cells in said cell containing sample.

2. The method of claim 1, wherein said cells are T cells.

3. The method of claim 1, wherein said I-309 is a mammalian I-309.

4. The method of claim 1, wherein said I-309 is administered in an amount ranging from about 0.1 ng/ml to about 100 ng/ml.

5. The method of claim 4, wherein said I-309 is administered in an amount ranging from about 1.0 ng/ml to about 3.0 ng/ml.

6. The method of claim 1, comprising administering said I-309 to a subject in vivo.

7. The method of claim 1, comprising administering said I-309 to a culture of cells in vitro.

8. A method for enhancing cell apoptosis comprising administering to a cell sample containing I-309 β chemokine an amount of an I-309 inhibitor sufficient to enhance apoptosis of cells in said sample.

9. The method of claim 8, wherein said inhibitor is an antibody which specifically binds to said I-309.

* * * * *